United States Patent [19]
Fletcher et al.

[11] 3,971,364
[45] July 27, 1976

[54] CATHETER TIP FORCE TRANSDUCER FOR CARDIOVASCULAR RESEARCH

[76] Inventors: James C. Fletcher, Administrator of the National Aeronautics and Space Administration, with respect to an invention of Cyril Feldstein, Sierra Madre; Gilbert W. Lewis, Arcadia; Robert H. Silver, Van Nuys; Virgil H. Culler, La Canada, all of Calif.

[22] Filed: May 16, 1975

[21] Appl. No.: 578,241

[52] U.S. Cl. ............................. 128/2 S; 128/2.05 E; 128/2.06 E; 128/418; 128/419 P; 73/398 AR
[51] Int. Cl.² .......................................... A61B 5/10
[58] Field of Search ............. 128/2, 2.05, 2.06, 418, 128/419; 73/398

[56] References Cited
UNITED STATES PATENTS

| | | | |
|---|---|---|---|
| 3,474,776 | 10/1969 | O'Brien | 128/2 S |
| 3,703,099 | 11/1972 | Rouse | 128/2.05 E X |
| 3,710,781 | 1/1973 | Hutchins et al. | 128/2.05 D |
| 3,750,650 | 8/1973 | Ruttgers | 128/2.06 E |
| 3,815,611 | 6/1974 | Denniston | 128/419 D |
| 3,831,588 | 8/1974 | Rindner | 128/2.05 E |

*Primary Examiner*—Delbert B. Lowe
*Attorney, Agent, or Firm*—Monte F. Mott; Wilfred Grifka; John R. Manning

[57] ABSTRACT

A force transducer for measuring dynamic force activity within the heart of a subject essentially consists of a U-shaped beam of low elastic compliance material. Two tines extend from the beam's legs and a long coil spring is attached to the beam. A strain gauge is coupled to one of the beam's legs to sense deflections thereof. The beam with the tines and most of the spring are surrounded by a flexible tube, defining a catheter, which is insertable into a subject's heart through an appropriate artery. The tines are extractable from the catheter for implantation into the myocardium by pushing on the end of the spring which extends beyond the external end of the catheter. The tines are retractable back into the catheter, prior to catheter removal from the subject, by pulling on the externally exposed spring end.

9 Claims, 3 Drawing Figures

CATHETER TIP FORCE TRANSDUCER FOR CARDIOVASCULAR RESEARCH

ORIGIN OF THE INVENTION

The invention described herein was made in the performance of work under a NASA contract and is subject to the provisions of Section 305 of the National Aeronautics and Space Act of 1958; Public Law 85-568 (72 Stat. 435; 42 USC 2457).

BACKGROUND OF THE INVENTION

1. Field of the Invention:

The present invention generally relates to a force transducer and, more particularly, to a force transducer to record dynamic force activity within the heart.

2. Description of the Prior Art:

A major thrust of heart research at present is directed towards the assessment of regional myocardial mechanics. For the enhancement of such research, force transducers, capable of recording dynamic force activity within the heart, are needed. It is particularly desirable to record such activity without having to open the chest. Although various force transducers are available none of them can be inserted into the heart to perform the desired measurements.

OBJECTS AND SUMMARY OF THE INVENTION

It is a primary object of the present invention to provide a new force transducer, finding particular utility in cardiovascular research.

Another object of the present invention is to provide a novel force transducer, insertable into the heart, without opening the chest, for recording dynamic force activity within the heart.

These and other objects of the invention are achieved by providing a very small force transducer, consisting essentially of a U-shaped beam of low elastic compliance. Sharp tines are rigidly attached to the ends of the U-shaped beam and a silicon semiconductor sensing element is attached to one of the legs or sides of the beam. One end of a long coil spring extends from the beam. The beam with the spring are placed in a hollow plastic tube, representing a catheter.

In use, the catheter, which surrounds the entire beam and the tines extending therefrom is inserted through an incision made through the skin of a subject into an artery and manipulated into one of the heart's chamber, e.g., the left ventricle. Once the catheter is in the appropriate heart chamber the beam is pushed out of the catheter far enough that the tines are fully implanted through the endocardium into the interior fibers of the myocardium. The leads from the sensing element extend through the catheter's external end (the end remaining outside the subject) and are connected to an appropriate recorder, e.g., an oscillograph. The beam is pushed out from the catheter, for insertion into the myocardium interior fibers, by pushing on the spring extending from the catheter's external end, while extraction of the tines from the myocardium and reinsertion of the beam into the catheter is achieved by pulling on the external end of the spring. By rotating the external end of the spring, measurements of force along different directions in the myocardium are easily attainable.

The novel features of the invention are set forth with particularity in the appended claims. The invention will best be understood from the following description when read in conjunction with the accompanying drawings.

DESCRIPTION OF THE PREFERRED EMBODIMENTS

Figure 1:
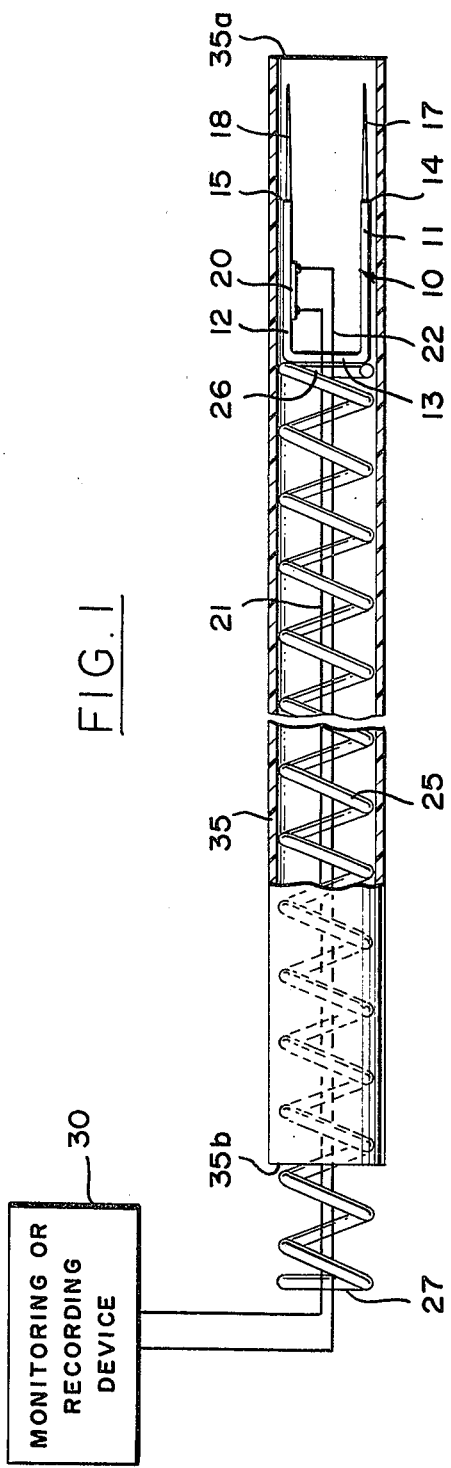
FIG. 1 is substantially a side view of the novel catheter.

Attention is directed to FIG. 1 wherein the novel transducer is shown including a U-shaped beam 10 of low elastic compliance. The beam can be thought of as formed of two parallel spaced apart legs 11 and 12 which are interconnected at one end by a cross member 13. The other ends of the two legs, remote from cross member 13, are designated by numerals 14 and 15. Rigidly attached to the beam legs at ends 14 and 15 are two sharp tines 17 and 18. The tines are parallel to one another and extend in a direction away from cross member 13. If desired the outer ends 14 and 15 of the legs may be tapered to form sharp tips and thereby eliminate the need for tines 17 and 18. In such a case the legs would function as the tines. A strain gauge sensing element 20 is attached to one of the legs, such as leg 12. Electrical leads 21 and 22 extend from opposite ends of the sensing element 20.

Coupled to the cross member 13 of the U-shaped beam 10 is a long coil spring 25. The spring extends from an end 26, which is connected to cross member 13 of the beam 10, to an opposite end 27. In FIG. 1, the electrical leads 21 and 22 are shown extending from the sensor element 20 through the spring 25 and therefrom the leads extend to an appropriate monitoring or recording device, designated by numeral 30. The function of the latter is to display and/or record the changes in resistance of sensor element 20 which are caused by deflections of the leg 12 due to forces applied to the tine 18 when the latter is inserted into a muscle, subjected to dynamic forces, as will be described hereinafter.

As shown in FIG. 1 the transducer also includes a hollow plastic tube 35, hereinafter referred to as the catheter, which surrounds the beam 10, the tines 17 and 18 and practically all of the spring 25. The beam 10 and the spring are of such small size that they can be inserted within a catheter of sufficiently small diameter, of the type capable of being guided through an artery to a selected chamber of the heart of a subject, used in medical research. Generally, catheters of diameters on the order of several mm are used for such purposes. In one embodiment actually reduced to practice the catheter was a 7 french catheter of a diameter on the order of 2.3mm. The spacing between tines 17 and 18 was on the order of 1.5mm.

In FIG. 1 the catheter's ends are designated by 35a and 35b. End 35a is the front end or distal tip which is inserted through the appropriate artery from an incision of the skin of the subject to the desired heart chamber, while end 35b represents the catheter external end or proximal tip which remains outside the subject. The catheter 35 is long enough, e.g., 100cm, to enable end 35a to extend into the subject's heart, while end 35b remains outside the subject. Similarly spring 25 and leads 21 and 22 are long enough to extend through the entire length of the catheter as well as extend beyond external end 35b. The portion of the spring 25 extending beyond end 35b is used to manipulate the U-shaped beam 10, as will be described hereinafter. Leads 21 and 22 extend beyond end 35b to the device 30.

Figure 2:
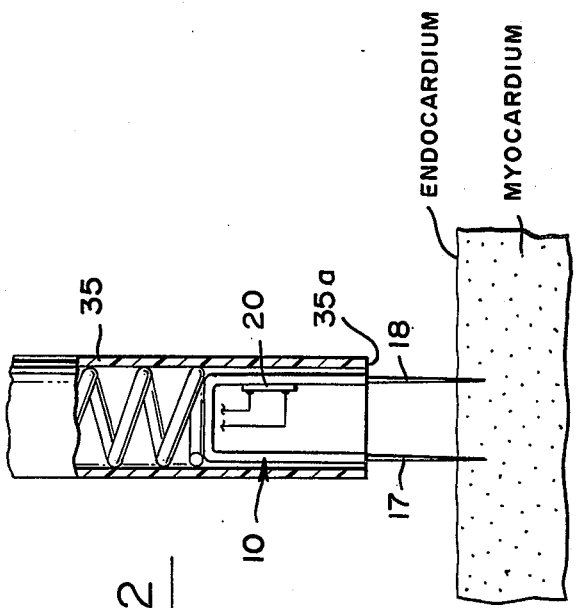
FIG. 2 is a diagram useful in explaining the use of the catheter.

In use, the catheter 35 is inserted into the subject's heart through an appropriate artery, with the beam 10 and tines 17 and 18 surrounded by the catheter, as shown in FIG. 1. In this position the tines cannot pierce or otherwise injure the artery during the catheter's insertion. Verification of the catheter's positioning near the endocardium of the heart at the appropriate location, where measurements are to be made, is achieved by fluoroscopy. Once the catheter is at the desired position the beam 10 together with the tines 17 and 18 are pushed foward so that the tines 17 and 18 extend beyond catheter end 35a and are implanted through the endocardium into the interior fibers of the myocardium; as shown in FIG. 2. Although not necessary, if desired, the entire beam 10 may be pushed out or withdrawn out of the catheter through fron end 35a. Dynamic forces in the myocardium deflect tine 18 and therefore leg 12 to which element 20 is connected. Its change in resistance which is proportional to the dynamic forces is transmitted via leads 21 and 22 to device 30 for monitoring or recording, in a manner well known in the art.

The extraction or removal of the tines from the catheter is easily achieved in the novel transducer of the present invention by pushing the portion of spring 25 which extends beyond the catheter external end 35b toward the catheter, thereby compressing the spring. The compressional force is transmitted through the spring coils to the beam 10 which is in turn pushed forward toward tip 35a, thereby exposing the tines which penetrate the myocardium through the endocardium. After performing the force measurement the tines are easily retracted back into the catheter by pulling on the externally exposed portion of the spring.

With the novel transducer of the present invention measurements of forces along different directions within the myocardium can be accomplished. After one measurement is made in which the tines are aligned in a first direction the spring is pulled back to extract the tines from the myocardium. Then the spring is rotated to align the tines in a different, second direction and thereafter the spring is pushed in to cause the tines to penetrate the myocardium, while being aligned in the second direction. Thus, the spring is most useful for the removal of the tines from the catheter for implanting into the myocardium, for retracting the tines back into the catheter after all measurements are made, as well as to align the tines so as to measure forces along different directions within the myocardium.

It should be pointed out that by using tines 17 and 18, beam 10 as well as the spring 25 all of which are of electrically conductive metals, the transducer can be used as an internal electrode for an electrocardiogram. Clearly, to this end spring end 26 need be attached to beam 10 and tines 17 and 18 need be attached to the beam's legs by means of electrically conductive joints such as by soldering or welding. To prevent electrical shock of the subject the leg 12 to which element 20 is attached may be covered by a layer of insulating material, such as epoxy. Also, the cross member 13 of beam 10 and one or more loops of the spring 25 near end 26 may be coated with epoxy to provide physical strength to the spring-beam interconnection.

From the foregoing it should thus be appreciated that with the novel invention disclosed herein forces in the myocardium can be measured without having to open the chest of the subject, i.e., without surgical intervention. The catheter is insertable into the heart through an artery extending from adjacent the subject's skin to the heart. Once the catheter front end is in the heart near the myocardium where force measurements are to be performed, tines are extracted from the catheter and penetrate the myocardium, by pushing on a coil spring which is surrounded by the catheter and extends beyond its external end or proximal tip. After measurements are made the tines are retracted back into the catheter by pulling on the spring before the catheter is removed from the subject.

It should be appreciated that although the invention has been described in connection with measuring forces in the myocardium of a subject the invention is not intended to be limited thereto. For example, the transducer may be inserted into a subject's stomach to measure forces in the stomach wall. In general the invention can be used to measure forces in any internal muscle which can be reached from the subject's skin without resort to surgery.

Figure 3:
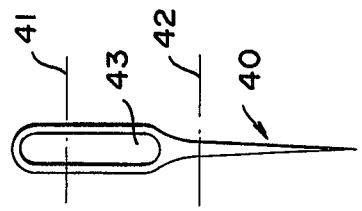
FIG. 3 is a diagram useful in explaining the formation of a U-shaped beam from a simple small needle.

It should be apparent that the small size U-shaped beam 10 may be machined from a block of metal or fabricated in any other conventional manner to form legs 11 and 12 connected by cross-member 13. In one embodiment, actually reduced to practice, the U-shaped beam consisted of a portion of a sewing needle, designated in FIG. 3 by numeral 40, which was cut off along lines 41 and 42. Thus, the U-shaped beam 10 consisted of a portion of the needle's eye 43.

Although particular embodiments of the invention have been described and illustrated herein, it is recognized that modifications and variations may readily occur to those skilled in the art, and, consequently, it is intended that the claims be interpreted to cover such modifications and equivalents.

What is claimed is:

1. A transducer for measuring forces in an internal muscle of a living subject without surgical intervention comprising:

first means including a plurality of substantially parallel spaced apart tines with tapered outer ends for penetrating an internal muscle of a subject;

strain gauge means coupled to said first means to provide an output related to the low compliance deflection of one of said tines;

an elongated flexible member having a first end coupled to said first means remote from said tines and extending to a second end; and an elongated flexible hollow tube, definig a catheter, having a first working end and an opposite second end, said catheter being adapted to be inserted into said subject so that its first end is substantially adjacent an internal muscle of said subject and the second end remaining external thereof, said catheter surrounding said first means with the tines adjacent and directed toward the catheter first end, and said elongated flexible member, except for a portion thereof, extending beyond said catheter second end, at least portions of said tines being extractable from said catheter first end for implantation in said muscle by pushing on the portion of the flexible member extending beyond said catheter second end toward said catheter, said tines being retractable from said muscle into said catheter through the first end thereof by pulling on the portion of the flexible member extending beyond said catheter second end.

2. The transducer as described in claim 1 wherein said flexible elongated member is a coil spring.

3. The transducer as described in claim 2 wherein said catheter is of a diameter on the order of several millimeters and said muscle is the myocardium of said subject, with said catheter, with the spring and said first means therein, being insertable into the subject's heart through an artery extending from adjacent the subject's external surface to said heart, with the catheter's second end and the portion of the spring extending outwardly therefrom remaining external to the subject's external surface.

4. The transducer as described in claim 2 wherein said strain gauge means include a pair of electrical leads extending from said strain gauge means through said catheter and beyond the second end thereof.

5. The transducer as described in claim 2 wherein said first means comprises a substantially U-shaped beam of low elastic compliance material and defining a pair of spaced apart legs terminating in tapered outer ends, defining said tines, and connected at their opposite end by a cross member, and means for coupling said first end of said spring to said cross member of said U-shaped beam.

6. A transducer for measuring forces in the myocardium of a living subject without resort to open chest surgery, comprising:

a U-shaped beam of low compliance material, defining a pair of spaced apart legs terminating in tapered outer ends, defining a pair of tines, and connected at their opposite ends by a cross member;

strain gauge means including a strain gauge in contact with one of said legs and a pair of long electrical wires connected to opposite ends of said strain gauge;

an elongated flexible member having a first end coupled to said beam cross member and extending to a second end; and an elongated flexible hollow tube, defining a catheter and having a first open end and an opposite second open end, said tube surrounding said U-shaped beam, with the strain gauge means, and said flexible member, with the tapered outer ends of the beam's legs pointing toward the first open end of said tube, and a portion of said elongated flexible member up to the second end thereof extending beyond the second open end of said tube, with portions of the electrical wires extending beyond the second open end of said tube, said tines being extractable out of the tube's first open end by pushing on the portion of the elongated member extending beyond the tube's second end, with said tines being retractable into said tube through its first open end by pulling on the portion of the elongated member extending beyond the tube's second open end.

7. The transducer as described in claim 6 wherein said elongated flexible member is a coil spring.

8. The transducer as described in claim 7 wherein said beam and said spring are of electrically conductive materials and electrically conductive means for connecting the first end of said electrically conductive spring to the electrically conductive cross member of said beam, whereby an electric path is provided from said tines to the second end of said spring which extends beyond the tube's second open end.

9. A method of measuring forces in the myocardium of a subject the steps comprising:

providing a transducer comprising a hollow elongated flexible tube having a first open end and an opposite second open end, said tube surrounding a U-shaped beam of low compliance material and defining a pair of spaced apart parallel legs with tapered outer ends, definig a pair of tines, said legs being connected at their opposite ends by a cross member of said beam, with the tines pointing toward the tube's first open end, said tube further surrounding a strain gauge connected to one of said legs and a pair of electrical leads connected to said strain gauge and extending through said tube and beyond the second open end thereof, said tube further surrounding an elongated coil spring, connected at a first end thereof to the beam cross member, with a portion of the spring up to a second end thereof extending beyond the tube's second open end;

inserting a portion of the tube extending from the first end thereof into the heart of a subject through an artery extending from adjacent the skin of said subject to said heart until the first end of said tube is adjacent the myocardium where force measurements are to be made, with a portion of the tube up to its second end remaining external to said subject;

pushing on the portion of the spring extending beyond the tube's second end to thereby extract the tines from the tube through the first end thereof and implant said tines in the myocardium; and measuring the output of said strain gauge across said electrical leads which is a function of the low compliance deflection of the leg to which said strain gauge is connected due to forces in said muscle applied to the leg's tine, said tines being extractable from said myocardium and retractable into said tube by pulling on the portion of the spring extending beyond the tube's second end which is external to said subject.

* * * * *